United States Patent [19]

Burrington et al.

[11] Patent Number: 4,604,244

[45] Date of Patent: Aug. 5, 1986

[54] PROCESS FOR MAKING ADIPONITRILE PRECURSORS

[75] Inventors: James D. Burrington, Richmond Hts.; Robert K. Grasselli, Aurora, both of Ohio; Craig T. Kartisek, Eugene, Oreg.

[73] Assignee: The Standard Oil Company, Cleveland, Ohio

[21] Appl. No.: 603,257

[22] Filed: Apr. 23, 1984

Related U.S. Application Data

[63] Continuation-in-part of Ser. No. 455,081, Jan. 3, 1983, abandoned.

[51] Int. Cl.$^4$ ................. C07C 120/00; C07C 120/14; C07C 121/30
[52] U.S. Cl. ..................................... 558/320; 558/311; 558/457
[58] Field of Search ............... 260/465.4, 465.8 R, 260/465.3, 465.8 D; 585/624

[56] References Cited

U.S. PATENT DOCUMENTS

| | | | |
|---|---|---|---|
| 3,342,849 | 9/1967 | Brill et al. | 260/465.3 |
| 3,345,397 | 10/1967 | Finley | 260/465.3 |
| 3,412,134 | 11/1968 | Jones | 260/465.3 X |
| 3,439,058 | 4/1969 | Bailey et al. | 585/624 X |
| 3,476,824 | 11/1969 | Woskow | 585/624 X |
| 3,551,470 | 12/1970 | Shaw et al. | 585/624 X |
| 3,658,877 | 4/1972 | Callahan et al. | 585/624 X |
| 3,819,679 | 6/1974 | Sheely | 260/465.3 |
| 3,932,551 | 1/1976 | Grasselli et al. | 585/624 |
| 3,944,592 | 3/1976 | Sheely | 260/465.3 |
| 4,246,191 | 1/1981 | Pujado | 260/465.3 |
| 4,246,192 | 1/1981 | Pujado | 260/465.3 |
| 4,413,155 | 11/1983 | Suresh et al. | 585/624 X |
| 4,436,671 | 3/1984 | Furuoya et al. | 260/465.3 |

FOREIGN PATENT DOCUMENTS 1394207  5/1975  United Kingdom.

Primary Examiner—Joseph Paul Brust
Attorney, Agent, or Firm—Charles S. Lynch; John E. Miller; Larry W. Evans

[57] ABSTRACT

Disclosed is the reaction of propylene with acrylonitrile or acrylamide to make a cyano- or amidopentene and reacting that compound with $NH_3$ and $O_2$ to form mucononitrile or 5-cyano-2,4-pentadiene amide. Also disclosed is a process which comprises contacting a reactant of the formula $H-(CH_2)_a-(CH=CH)-(CH_2)_bX$ with oxygen and ammonia to thereby form a product of the formula $NC-CH=CH-CH=CH-X$ wherein X is $-CN$ or $-CONH_2$ and each of a and b are zero or an integer from 1 to 3 such that $a+b=3$.

8 Claims, No Drawings

PROCESS FOR MAKING ADIPONITRILE PRECURSORS

This application is a continuation-in-part of application Ser. No. 455,081, filed Jan. 3, 1983, now abandoned.

In one aspect the present invention relates to an improved process for making unsaturated nitriles. In a particular aspect, the invention relates to a novel process for making mucononitrile, easily converted to adiponitrile.

One of the basic raw materials in the production of nylon-6,6 is hexamethylenediamine. Commercially, hexamethylenediamine is produced by the catalytic hydrogenation of adiponitrile (1,4-dicyanobutane). Adiponitrile, in turn, is produced commercially in a variety of different ways including the reaction of butadiene with chlorine and then HCN and then hydrogen, the electrohydrodimerization of acrylonitrile and the direct hydrocyanation of butadiene. Other processes have also been proposed.

Each of these processes is disadvantageous for one reason or another.

Accordingly, it an object of the present invention of provide a new process for producing an adiponitrile precursor which is simple and straightforward to carry out.

In addition, it a further object of the present invention to provide a new process for producing an adiponitrile precursor which employs readily available starting materials.

Other objects, as well as aspects and advantages, of the invention will become apparent from a study of the disclosure, the examples and the claims.

These and other objects are accomplished by the invention in accordance with which mucononitrile, an adiponitrile precursor, is produced by a two step process in which acrylonitrile and propylene are reacted to form 5-cyanopentene-1 and thereafter the 5-cyanopentene-1 is reacted with $NH_3$ and molecular oxygen to make mucononitrile. Mucononitrile is easily hydrogenated by known processes to form adiponitrile.

The first reaction can also be used to produce a 5-amidopentene-1 by using the corresponding analogous reactants. If, instead of acrylonitrile in the first reaction acrylamide is reacted with propylene, the product is 5-amidopentene-1. Then in the second step the last named compound is reacted with $NH_3$ and molecular oxygen as before, but the product is 5-cyano-2,4-pentadiene amide. The ensuing discussion is described in terms of propylene and acrylonitrile but is equally applicable to using propylene and acrylamide as the starting materials.

In a specific aspect of the invention there is provided a novel process for producing an adiponitrile precursor comprising reacting propylene and acrylonitrile in a first reaction, referred to hereinafter as the "ene" reaction, to form 5-cyanopentene-1. Next, 5-cyanopentene-1 is reacted with $NH_3$ and oxygen to form mucononitrile. Finally, the mucononitrile product of the invention can be catalytically hydrogenated to adiponitrile by known processes. The reaction scheme is given as follows:

$$CH_2=CH-CH_3 + CH_2=CH-CN \longrightarrow \quad (1)$$

propylene     acrylonitrile

-continued $$CH_2=CH-CH_2-CH_2-CH_2-CN$$

5-cyanopentene-1

$$CH_2=CH-CH_2-CH_2-CH_2-CN + NH_3 + 2O_2 \longrightarrow \quad (2)$$

5-cyanopentene-1

$$NC-CH=CH-CH=CH-CN + 4H_2O$$

mucononitrile $$NC-CH=CH-CH=CH-CN + 2H_2 \longrightarrow \quad (3)$$

mucononitrile $$NC-CH_2-CH_2-CH_2-CH_2-CN$$

adiponitrile

The first step of the inventive reaction scheme given above is known and described, for example, in the following references, the disclosures of which are incorporated herein by reference: Albisetti, C., J. C. Fisher, N. G., Hogsed, M. J., and Joyce, R. M., *J. Amer. Chem. Soc,*. 1956, 78, 2637. See also U.S. Pat. Nos. 3,840,583, 3,898,268, 3,966,798 and 3,996,262.

When using acrylamide in reaction (1) instead of acrylonitrile, the reaction scheme is as follows:

$$CH_2=CH-CH_3+CH_2=CH-CONH_2 \rightarrow CH_2=CH-CH_2-CH_2-CH_2CONH_2 \quad (4)$$

$$CH_2=CH-CH_2-CH_2-CH_2-CONH_2+NH_3 \\ +2O_2 \rightarrow NC-CH=CH-CH=CHCONH_2+4-H_2O \quad (5)$$

The conjugated cyano-amido diene can then be hydrogenated to $NC-CH_2-CH_2-CH_2-CH_2-CONH_2$, 5-cyanovaleramide.

Thus, according to one aspect of the invention there is provided a process which comprises (a) reacting propylene with an enophile of the formula:

$$CH_2=CH-X$$

wherein
X is $-CN$ or $-CONH_2$
to form a cyano- or amidoalkene of the formula:

$$CH_2=CH-(CH_2)_3-X, \text{ and}$$

(b) reacting said amido- or cyanoalkene with $NH_3$ and molecular oxygen to form a product of the formula:

$$NC(CH=CH)_2-X$$

Reaction (1) or (4), known as the "ene" reaction, can be accomplished in the absence of a catalyst as shown in the above Albisetti article or using various different catalysts. In accordance with the present invention, the ene reaction using propylene and acrylonitrile or acrylamide as reactants is carried out using a Lewis acid as the catalyst.

Lewis acids are well known and defined as any compound that can easily form a stable complex by accepting an electron pair from another compound or substance.

Especially useful Lewis acids used in the "ene" reaction step of our invention have the following formula:

$$R_aM^xX_b$$

wherein

R is alkyl, alkyloxy, aryl, or aryloxy having no more than 15 carbon atoms, said aryl groups containing only C and H, M is a metal selected from B, Al, Gn, In, Tl, P, As, Sb, Bi, Si, Ge, Pb, Ti, Zr and Hf, and X is Cl, B, F or I, and further wherein x represents the valence of M and is 3, 4 or 5, a is 0, 1, 2, 3, 4 or 5, b is 1, 2, 3, 4 or 5 with the proviso that b can be 0 when M is B, Al, Gn, In or Tl, and $a+b=x$ Representative examples of suitable Lewis acids are: $BBr_3$, $BCl_3$, $SbCl_5$, $AlCl_3$, $FeCl_3$, $BF_3$, $ZrBr_2$, $EtAlCl_2$, $TiCl_4$, $Et_2AlCl$ and $SnCl_4$, wherein "Et" refers to the ethyl group. Thus, $Et_2AlCl$ is diethylaluminum chloride.

The ene reaction can be carried out either homogeneously (i.e. in the liquid phase in batch operation) or heterogeneously (i.e. gaseous reactants contacting solid catalysts). In the homogeneous mode, reaction times of 0.1 second to 120 hours can be used, although reaction times on the order of 0.5 to 48 hours are preferred. In the heterogeneous mode, contact times on the order of 0.5 to 30 seconds are useful. In either mode, reaction temperatures on the order of 0° to 600° C., preferably 100° to 300° C., more preferably 150° to 250° C., can be employed and reaction pressures of 1 to 1000 atm, preferably 1 to 250 psi can be employed.

The amount of acrylonitrile or acrylamide employed in the ene reaction can vary widely. In homogeneous operation, it can be present in the liquid reaction system in amounts from $10^{-4}$ to 15.1 molar, preferably $10^{-3}$ to 15 molar. In heterogeneous operation, throughput of acrylonitrile or acrylamide can be from $10^{-5}$ to 1, preferably $10^{-4}$ to 1, more preferably $10^{-2}$ to $10^{-1}$, throughput being measured as WWH, which is defined as weight of reactant fed per unit weight of catalyst per hour.

Typically the amount of catalyst used in the homogeneous reaction will be such that the catalyst/acrylonitrile or acrylamide molar ratio is $10^{-4}$:1 to $10^2$:1, preferably $10^{-3}$:1 to 10:1, more preferably 0.05:1 to 0.5:1.

Finally, the amount of propylene used in the reaction system can also vary widely and is normally such that the molar ratio of acrylonitrile or acrylamide to propylene is in the range $10^{-4}$ to $10^3$, more preferably 0.1 to 10.

The ene reaction can be carried out in the presence or absence of a solvent. Suitable solvents are acetonitrile, acetone, isopropyl alcohol, toluene, chlorobenzene, methanol, nitrobenzene and dimethylformamide. Nitrobenzene is especially efficacious.

The product of the ene reaction, 5-cyanopentene-1 or 5-amidopentene-1 can be recovered from the gross reaction product by distillation to remove the reactants and solvent, if any. When the process is conducted in the homogeneous mode, the gross reaction product can be filtered to remove any solid materials before the distillation procedure.

In the present inventive process reaction (2) or reaction (5), in which a cyanopentene or a amidopentene is reacted with $NH_3$ and oxygen, is conveniently referred to as an ammoxidation reaction. It is, however, not a simple ammoxidation reaction but is an ammoxidation reaction which is effected simultaneously with an oxydehydrogenation reaction, wherein both a terminal nitrile group and a second C=C group are formed to yield the conjugated diene structure of mucononitrile or of the cyano-amido product.

Thus, in accordance with one aspect of the invention there is provided a process which comprises contacting a reactant of the formula:

$$H—(CH_2)_a—(CH=CH)—(CH_2)_bX$$

with oxygen and ammonia to thereby form a product of the formula:

$$NC—CH=CH—CH=CH—X$$

wherein

X is —CN or —CONH$_2$, and each of a and b are zero or an integer from 1 to 3 such that $a+b=3$.

The overall reaction is as follows:

$$H(CH_2)_a—CH=CH—(CH_2)_bX+2O_2+NH_3\rightarrow$$
$$NC—CH=CH—CH=CH—X+4H_2O \qquad (6)$$

where X is —CN or —CONH$_2$ and where each of a and b is zero or an integer from 1 to 3 and $a+b=3$.

In an important aspect of the invention X is —CN. When X is —CN and the starting reactant is 5-cyanopentene-1, the reaction is reaction (2).

When the starting material in reaction (6) is 5-cyanopentene-2, 1-cyanopentene-3 or 1-cyanopentene-2 the product is the same mucononitrile.

When the reactant is 5-amidopentene-1, 5-amidopentene-2, 1-amidopentene-3, or 1-amidopentene-2 and is reacted with one mole of $NH_3$ and 2 moles of $O_2$ the product is $$NC—CH=CH—CH=CH—CONH_2+4H_2O.$$

It is believed that the inventive "ammoxidation" reactions were not known before our invention thereof and we regard the reaction per se as a broad aspect of our invention.

Catalysts are useful in the present "ammoxidation" process and in one aspect of the present invention the ammoxidation-oxydehydrogenation reaction of the present invention is effected by contact of the reactants shown in the equations with any solid oxidation catalyst which is effective to catalyze the ammoxidation of propylene to acrylonitrile.

The ammoxidation of unsaturated compounds such as propylene is a well known reaction and is described, for example, in the following articles: Grasselli, R. K., Burrington, J. D., "Selective Oxidation and Ammoxidation of Propylene by Heterogeneous Catalysis", pp133–163, *Advances in Catalysis*, Vol 30, copyright 1981, Academic Press Inc.; Tedder, Nechvatal, Jub, *Basic Organic Chemistry*, pp265–270, copyright 1978, Verlag Chemie GmbH. The reaction is accomplished by contacting the reactants with an ammoxidation catalyst under suitable conditions. Representative examples of such catalysts useful in the present invention are bismuth molybdates, the metal antimonates of metals selected from iron, tin, uranium, manganese, vanadium and tungsten, cadmium tellurates and so forth. Such catalysts are very well known and have been promoted with a large number of naturally occurring elements. Such catalysts are illustrated, for example, in the following U.S. Pat. Nos.: 2,904,580; 3,766,092; 3,642,930; GB Pat. No. 1,478,621; U.S. Pat. Nos. 4,192,776; 3,338,952; 3,431,292; 3,625,867 and 3,641,101.

Especially useful catalysts in the inventive ammoxidation reaction are oxide complex redox catalysts defined by the general formula:

$$A_a B_b C_c D_d O_x$$

wherein
A is an alkali metal, alkaline earth metal, Zn and/or Tl,
B is a Group VB metal, Fe, Ce, Te, Se, and/or U, preferably Bi and/or Sb,
C is Mo, W, Cr, Sb, Te, Se, V and/or P, and
D is Fe, Cr, Cu, Co, Ni, and/or Mn, and further
wherein
a is zero to 4,
b is zero to 10,
c equals 1,
d equals zero to 10, and
x is a number sufficient to satisfy the valence requirements of the other elements present.

Also especially useful are catalysts which are promoted or unpromoted bismuth molybdates, which when promoted contain one or more elements selected from Fe, P, As, Sb, Ni, Co, Mg, Cd, Cs, Ba, K, Rb, Cs, Mn, Sn, Cr, W, Tl, Ag, Nb, Ta, V and Cu. Such catalysts are conveniently defined by the following formula:

$$X_q Bi_r Mo_{12} O_x$$

wherein
X is one or more promoter element described above, and further
wherein
r is 0.3-11,
q is zero to 1.2(r+12), and
x is a number sufficient to satisfy the valence requirement of the other elements present.

The above catalysts can be used unsupported or in supported form. Any conventional support material such as silica can be used.

Normally the inventive ammoxidation reaction is carried out in the heterogeneous mode with the catalyst being in the solid phase and the reactants in the gaseous phase. The reaction temperature is normally between 250° to 650° C. As well appreciated by those skilled in the art, the minimum reaction temperature is determined by the reactivity of the system, i.e. when the temperature is too low, no reaction takes place. In addition, at temperatures which are too high, unwanted side reactions occur, specifically carbon monoxide and carbon dioxide are produced in large excess. The reaction temperature to use for a particular reactant and catalyst can be easily determined by routine experimentation based on the above considerations with reaction temperatures on the order of 350° to 500° C. being preferred and 400° to 460° C. being even more preferred.

Reaction pressures can also vary widely. Normally the reaction pressure will be 0.5 to 20 atmospheres, more preferably 1 to 10, even more preferably 1 to 3 atmospheres.

The reactant throughputs and reactant contact times can vary widely. Contact times on the order of 0.1 to 30 seconds are acceptable with contact times of 1 to 5, preferably 1.5 to 3 seconds being preferred. Throughputs on the order of $10^{-5}$ to 10, preferably $10^{-2}$ to 1, measured in terms of WWH, are acceptable.

The reactant feed ratios can also vary widely and essentially any feed ratios can be employed. For best results, the amounts of oxygen and ammonia should be slightly in excess of the stoichiometric amounts needed for complete reaction. There is, however, no lower or upper limit on the oxygen and ammonia feed ratios. Ordinarily, 1 to 10 moles of ammonia, preferably 1.1 to 1.5 moles of ammonia should be used for each mole of cyanopentene or amidopentene and 2 to 10 moles, preferably 2.5 to 4 moles oxygen used for each mole of amido- or cyanopentene. The reaction system can also employ inert carrier gases such as nitrogen, and indeed most typically air will be used to supply the oxygen.

After reaction, the gaseous gross reaction product can be recovered and purified in a conventional manner. For example, the gross reaction product can be scrubbed with water and distilled to recover purified mucononitrile or the cyano-amido diene.

The amido- and cyanopentene reactants for the ammoxidation reaction can be made in any suitable manner other than the ene reaction. For example, such compounds can be made by heating a mixture of the corresponding halogenated derivative with potassium cyanide at elevated temperature in a suitable solvent such as ethylene glycol. See, for example F. B. LaForge, N. Green and J. Gevsdortf, *J. Amer. Chem. Soc.*, 1948, 70, 3707, in which 5-cyanopentene is produced by heating a mixture containing 60 weight percent 5-bromo-1-pentene with potassium cyanide and ethylene glycol at 100° C.

The adiponitrile made by hydrogenation of the mucononitrile is not only a monomer for nylon, see U.S. Pat. Nos. 2,245,129 and 3,847,876, but is also useful in the manufacture of hexamethylenediamine (by hydrogenation) for use in making various polymers, especially nylon 6,6. The 5-cyanopentanedienoic amides products can be hydrogenated to $NC-CH_2-CH_2-CH_2-CH_2-CONH_2$, which can in turn be hydrogenated to hexamethylenediamine.

The hydrogenation of the ammoxidation products of the invention to saturate the C=C bonds thereof can be easily accomplished by the catalytic hydrogenation processes shown, for example, in the following references: Patterson, W. R., "Selective Hydrocarbon Oxidation" in *Catalysis and Chemical Processes*, Wiley, New York, 1981, 289; Stimek, R. T., and Rase, H. F., *Ind. Eng. Chem. Prod. Res. Dev.*, 1978, 17, 227; U.S. Pat. No. 4,311,859 (Phillips Petroleum Co.), Dec. 5, 1980.

For example, mucononitrile can be catalytically hydrogenated to adiponitrile by heterogeous gas/solid hydrogenation at ~260° C. using a Pd on C catalyst in a monomer similar to that described in the previously cited Rase, et al. reference.

The saturated dinitrile or 5-cyanovaleramide products can also be used to make various forms of nylon after converting the terminal cyano and/or amido groups to amino groups. This can be readily accomplished by hydrogenation reactions well known in the art. See, for example, Weissermel, K. and Arpe, H. J., "Industrial organic Chemistry", Verlag Chemie, 1978, New York, P. 219; U.S. Pat. No. 4,254,059 (Allied Chemical Corp.), Aug. 1, 1979. For example, adiponitrile can be readily converted to hexamethylenediamine by high pressure (600-650 bar) hydrogenation at 100°-135° C. with Co-Cu catalysts, or at low pressures (300-350 bar) at 100°-180° C. using Fe catalysts, as described in Arpe, et al. referenced above.

EXAMPLES

In order to more thoroughly describe the present invention, the following illustrative examples are presented, but are not to be taken as limiting.

COMPARATIVE EXAMPLE A—PRODUCTION OF 5—CYANOPENTENE—1

2.0 ml acrylonitrile (0.03 mole) and 4 ml nitrobenzene as solvent were deposited in a 300 ml pressure autoclave. Propylene was then condensed into the autoclave kept at −78° C. The autoclave was sealed and the contents were then heated to 240° C. The reaction temperature was maintained at 240° C. for 4 hours, during which time the reaction pressure was measured as 1500 psig. After 4 hours, heating was terminated, the autoclave was opened and the liquid reaction product recovered and purified by distillation. It was found that acrylonitrile conversion was 22 percent, selectivity to 5-cyanopentene-1 was 3.2 percent and the yield of 5-cyanopentene-1 was 0.7 percent.

For the purposes of this application:

$$\text{Conversion} = \frac{\text{Moles reactant reacted}}{\text{Moles reactant supplied}}$$

$$\text{Selectivity} = \frac{\text{Moles product formed}}{\text{Moles reactant reacted}}$$

$$\text{Yield} = \frac{\text{Moles product formed}}{\text{Moles reactant supplied}}$$

EXAMPLE 1

Comparative Example A was repeated except that the reaction medium included 0.1 equivalent $AlCl_3$ as a Lewis acid catalyst per equivalent of acrylonitrile. In addition, the reaction temperature was maintained at 200° C. rather than 240° C. In this example, it was found that acrylonitrile conversion was 53 percent, selectivity to 5-cyanopentene was 5.1 percent and 5-cyanopentene yield was 2.7 percent.

EXAMPLES 2 TO 4 AND COMPARATIVE EXAMPLE B

Acrylonitrile and propylene were converted to 5-cyanopentene in accordance with the general procedure used in Example 1 and Comparative Example A above. In these examples, however, 6.0 ml tetrohydrofuran was employed as the solvent, 2.0 ml acrylonitrile (0.03 mole) and 7.0 g propylene (0.167 mole) were employed as the reactants, the reaction pressure was 1250 psig and the reaction temperature was 225° C. Different catalysts were employed in the different examples. The identity of the catalysts and the results obtained are set forth in the following table:

TABLE 1

| Ex | Catalyst per Equiv. of Acrylo | Acrylo Conver. | Selectivity 5-cyano-pentene | 5-cyano-pentene Yield |
|---|---|---|---|---|
| B | None | 67 | 0.7 | 0.5 |
| 2 | 0.2 g* $AlCl_3$ | 39.1 | 2.0 | 0.8 |
| 3 | 0.3 g* $RuCl_3.3H_2O$ | 64 | 1.1 | 0.7 |
| 4 | 0.2 g $AlCl_3$/0.3 eq $RuCl_3.3H_2O$ | 80 | 2.5 | 2.0 |

*0.0015 mole

COMPARATIVE EXAMPLE C 2.0 ml acrylonitrile (0.03 mole) and 5.1 g propylene (0.121 mole) were charged into the autoclave. The autoclave was heated to 300° C. and maintained at that temperature for 4 hours, during which time the reaction pressure was 1500 psig. The gross reaction product was then recovered and analyzed. It was found that acrylonitrile conversion was 100 percent but that the selectivity and yield to 5-cyanopentene was zero.

The above examples show that alkenes and unsaturated nitriles can be converted to cyanoalkenes by simple and straight-forward procedures at low temperatures and pressures.

EXAMPLES 5 TO 13

A series of experiments was conducted in which 5-cyanopentenes were ammoxidized to produce mucononitrile. In each experiment, the reactant was composed of 54 percent 5-cyanopentene-1 and 46 percent 5-cyanopentene-2. In each experiment, a feed comprising 1.0 cyanopentene/1.2 $NH_3$/15.5 air/60 $N_2$ was contacted with 2.5 cc solid catalyst at a reaction temperature of 430° C. at a contact time of 2.0 seconds. The gross reaction product was recovered and analyzed to determine the amount of mucononitrile produced. The identities of the catalysts and results obtained are set forth in Table 2. In Example 5, an analysis of the unreacted cyanopentenes was made by gas chromatograph and it was found that it was 32 percent 5-cyanopentene-1, and 68 percent 5-cyanopentene-2, showing that both feed isomers reacted, although the 5-cyanopentene-1 reacted faster.

TABLE 2

| Ex | Catalyst Composition | 5-cyanopentene Conversion | Mucononitrile Yield |
|---|---|---|---|
| 5 | $Bi_2Mo_3O_x$ | 40.6 | 13.4 |
| 6 | $MoO_3$ | 26.0 | 5.9 |
| 7 | 50 $K_{0.1}Ni_{2.5}Co_{4.5}Fe_3BiP_{0.5}Mo_{12}O_x$—50 $SiO_2$ | 59.9 | 13.7 |
| 8 | 50 $Cs_{0.05}K_{0.1}Ni_{2.5}Co_{4.5}MnFe_2Cr_{0.5}BiMo_{13.2}O_x$—50 $SiO_2$ | 62.1 | 13.2 |
| 9 | 50 $Cs_{0.2}K_{0.1}Ni_{2.5}Co_{4.5}MnFe_2Cr_{0.5}BiMo_{13.2}O_x$—50 $SiO_2$ | 52.5 | 5.9 |
| 10 | $Cs_{0.05}Bi_2Mo_3O_x$ | 14.2 | 2.8 |
| 11 | $Bi_2MoO_x$ | 59.9 | 6.7 |
| 12 | 50 $Bi_2W_3O_{12}$—50 $SiO_2$ | 56.1 | 1.6 |
| 13 | 59 $V_{0.184}W_{0.097}Mo_{0.68}Cu_{3.83}Te_{1.63}Fe_{12}Sb_{24}O_x$—41 $SiO_2$ | 99.8 | 0.7 |

EXAMPLES 14 TO 21

Under the conditions of Example 5, including the same catalyst, but the feed being the amido or cyano compound listed in the first column of Table 3 instead of the 5-cyanopentene-1 and 5-cyanopentene-2 mixture, the products are as listed in the second column. It will be seen that the position of the double bonds in the product is the same regardless of the starting reactants.

TABLE 3

| Reactant | Product |
|---|---|
| 14. 1-cyanopentene-2 | mucononitrile |
| 15. 1-cyanopentene-3 | mucononitrile |
| 16. 5-cyanopentene-1 | mucononitrile |
| 17. 5-cyanopentene-2 | mucononitrile |
| 18. 1-amidopentene-2 | 5-cyano-2,4-pentadiene amide |
| 19. 1-amidopentene-3 | 5-cyano-2,4-pentadiene amide |
| 20. 5-amidopentene-1 | 5-cyano-2,4-pentadiene amide |
| 21. 5-amidopentene-2 | 5-cyano-2,4-pentadiene amide |

As will be evident to those skilled in the art various modifications of this invention can be made or followed in the light of the foregoing disclosure and discussion without departing from the spirit and scope of the disclosure of from the the scope of the claims.

We claim:

1. A process which comprises contacting a reactant of the formula:

$$H-(CH_2)_a-(CH=CH)-(CH_2)_bX$$

with oxygen and ammonia to thereby form a product of the formula:

$$NC-CH=CH-CH=CH-X$$

wherein
X is —CN or —CONH$_2$ and each of a and b are zero or an integer from 1 to 3 such that a+b=3, and wherein said contacting of said reactants is effected while said reactants (1) are in the gaseous phase and are in contact with a solid oxidation catalyst which is effective to catalyze the ammoxidation of propylene to acrylonitrile, and (2) are in the temperature range from 250° to 650° C.

2. A process of claim 1 wherein X is —CN and the product is mucononitrile.

3. A process of claim 2 wherein said reactant is $CH_3-CH=CH-CH_2CH_2CN$.

4. A process of claim 2 wherein said reactant is $CH_3-CH_2-CH=CH-CH_2CN$.

5. A process of claim 2 wherein said reactant is $CH_2=CH-CH_2-CH_2-CH_2CN$.

6. A process of claim 2 wherein the reaction contact time is 0.1 to 30 seconds.

7. A process which comprises:
(a) reacting propylene with an enophile of the formula:

$$CH_2=CH-X$$

wherein
X is —CN or —CONH$_2$ to form a cyano or amidoalkene intermediate of the formula:

$$CH_2=CH-(CH_2)_3-X, \text{ and}$$

(b) contacting and reacting said intermediate with molecular oxygen and ammonia to thereby form a product of the formula:

$$NC(CH=CH)_2-X$$

wherein
X is —CN or —CONH$_2$, and wherein said contact is effected while the reactants (1) are in the gaseous phase and are in contact with a solid oxidation catalyst which is effective to catalyze the ammoxidation of propylene to acrylonitrile, and (2) are in the temperature range from 250° to 650° C.

8. A process of claim 7 wherein X is —CN and the product is mucononitrile.

* * * * *